United States Patent [19]

Shoesmith, deceased

[11] Patent Number: Plant 6,400

[45] Date of Patent: Nov. 15, 1988

[54] CHRYSANTHEMUM PLANT NAMED BUCCANEER

[75] Inventor: Leonard H. Shoesmith, deceased, late of Westfield, England, by May Victoria Shoesmith, executrix

[73] Assignee: Ball Pan Am Plant Co., Parrish, Fla.

[21] Appl. No.: 5,851

[22] Filed: Jan. 21, 1987

[51] Int. Cl.[4] ..... A01H 5/00

[52] U.S. Cl. ..... Plt./74

[58] Field of Search ..... Plt./68, 74

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named Buccaneer characterized by its bright yellow floret color, double flower form; compact, freely branching growth habit, and by its 8½ week flowering response period.

1 Drawing Sheet

1

The present invention comprises a new and distinct cultivar of *Chrysanthemum morifolium,* Ramat., hereinafter referred to by the cultivar name Buccaneer.

Buccaneer is a product of a planned breeding program which had the objective of creating new Chrysanthemum cultivars having the characteristics of free branching, compact growth habit, bright yellow button flower, fast flowering response, and suitability both for greenhouse production in 4½" pots and as a garden mum. Such traits in combination were not present or needed improvement in previously available commercial cultivars.

Buccaneer was originated from a hybridization made in a controlled breeding program in Westfield-Woking, England by Leonard H. Shoesmith in 1980. The male and female parents are unknown at this time. Buccaneer was discovered and selected as one flowering plant within the progeny of the stated parentage by Leonard H. Shoesmith in November 1981 in a controlled environment in Parrish, Fla.

The first act of asexual reproduction of Buccaneer was accomplished when vegetative cuttings were taken from the initial selection in February 1982 in a controlled environment in Parrish, Fla. by a technician working under formulations established and supervised by Leonard H. Shoesmith. Horticultural examination of selected units initiated in April 1982 has demonstrated that the combination of characteristics as herein disclosed for Buccaneer are firmly fixed and are retained through successive generations of asexual reproduction.

Buccaneer has not been observed under all possible environmental conditions. The phenotype may vary significantly with variations in environment such as temperature, light intensity, and day length. The following observations, measurements and comparisons describe plants grown in Parrish, Fla. under greenhouse conditions which approximate those generally used in commercial practice.

The following traits have been repeatedly observed and are determined to be basic characteristics of Buccaneer, which in combination distinguish this chrysanthemum as a new and distinct cultivar:

1. Compact, freely branching growth habit, suitable for production as a garden mum or in 4½" pots.
2. Bright yellow flower color and double flower form.
3. Approximately 220 ray florets per capitulum.

2

4. Individual ray florets approximately 14 mm long×7 mm wide.
5. 8½ week flowering response period.
6. Approximately 34 mm across face of capitulum.

Of the many commercial cultivars known to the present inventor, the most similar in comparison to Buccaneer is Bingo, disclosed in a pending application of applicant. In comparison to Bingo, Buccaneer has a one week earlier flowering response, and is more freely branching (6 breaks for Buccaneer vs. 3 breaks for Bingo after one pinch). The color and flower shape of Buccaneer are similar to those same characteristics of Bingo.

The accompanying photographic drawing shows in perspective view typical inflorescence and foliage characteristics of Buccaneer. The drawing comprises a black and white photograph, with several flowers being colored to precisely depict flower color.

In the following description, color references are made to The Royal Horticultural Society Colour Chart. The color values were determined at approximately 4:00 p.m. on Aug. 27, 1986 under fluorescent light at Parrish, Fla.

Classification:

*Botanical.*—*Chrysanthemum morifolium,* Ramat., cv Buccaneer.

*Commercial.*—Garden mum.

INFLORESCENCE

A. Capitulum:

*Form.*—Flat.

*Type.*—Double.

*Diameter across face.*—32–35 mm.

B. Corolla of ray florets:

*Color (General tonality from a distance of three meters).*—Bright yellow.

*Color (upper surface).*—5A.

*Color (under surface).*—5B.

C. Corolla of disc florets:

*Color (mature).*—Yellow, very few.

*Color (immature).*—Yellow-green, very few.

D. Reproductive organs:

*Androecium.*—Present in disc florets only.

*Gynoecium.*—Present in ray and disc florets.

PLANT

A. General appearance:

*Height.*—20 cm when grown in a 4½" pot; height can vary depending upon growing conditions, B-Nine applications and cultural practices.

B. Foliage:

*Color* (*upper surface*).—147A.

*Color* (*under surface*).—147B.

*Shape.*—Ovate with cleft margins.

It is claimed:

1. A new and distinct cultivar of Chrysanthemum plant named Buccaneer, as described and illustrated, and particularly characterized by its bright yellow floret color, double flower form; compact, freely branching growth habit, and 8½ week flowering response period.

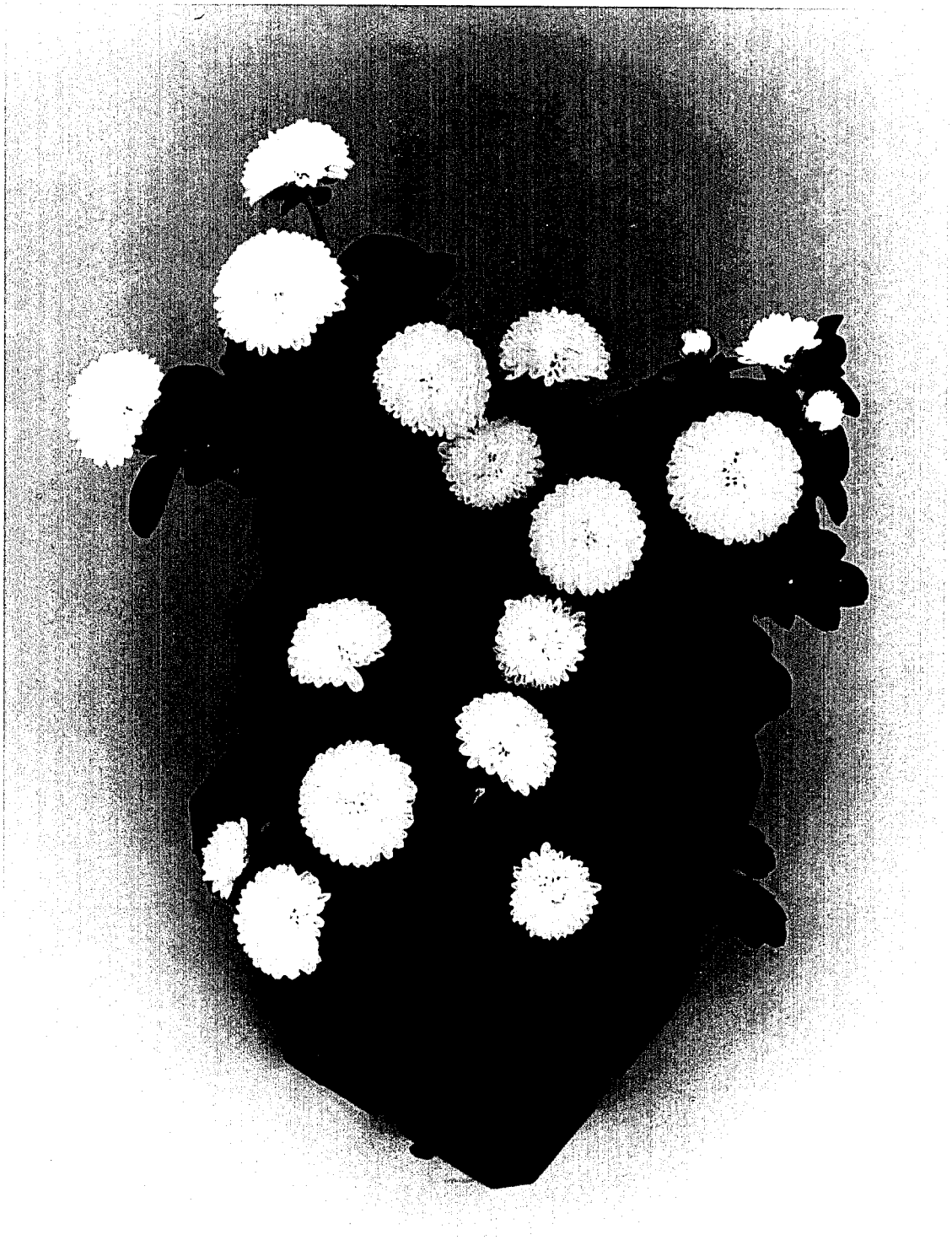

* * * * *